Aug. 4, 1959 M. COMBE Plant Pat. 1,856
ROSE PLANT
Filed Dec. 3, 1958
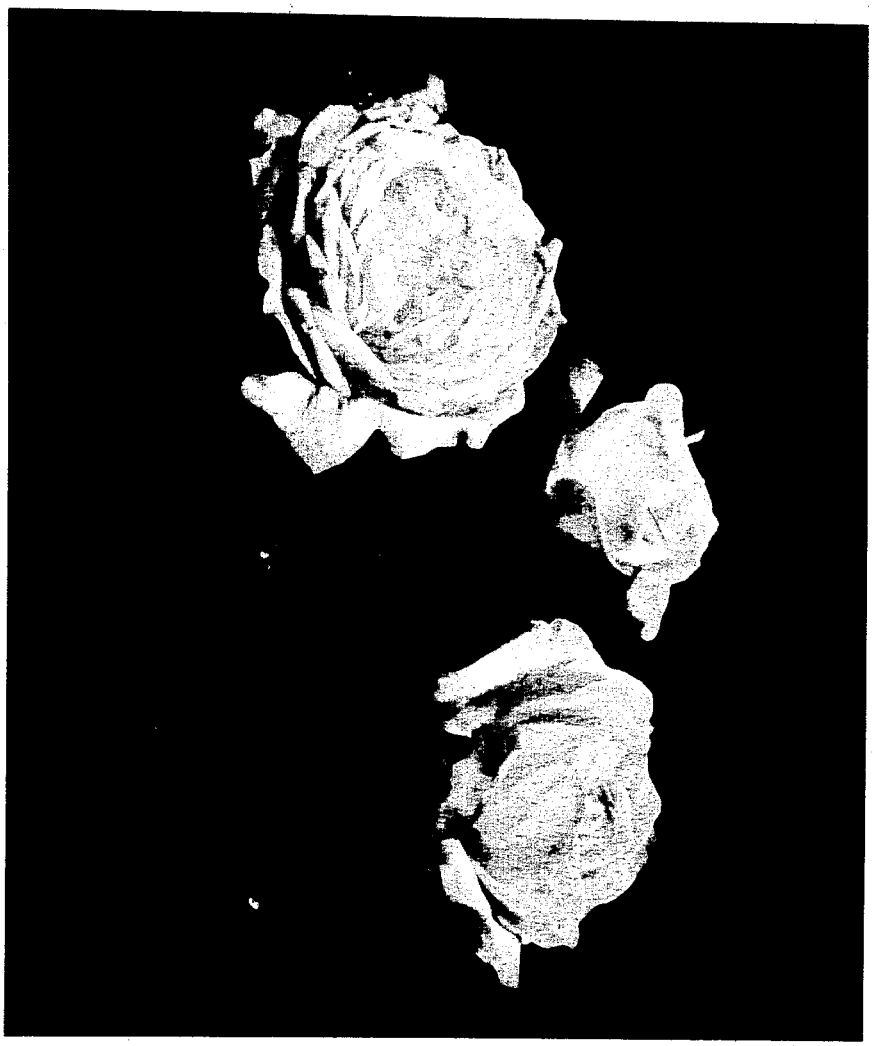
Inventor
Maurice Combe
By: Robbins Robb
Attorneys United States Patent Office Plant Pat. 1,856
Patented Aug. 4, 1959

1,856

ROSE PLANT

Maurice Combe, Grenoble, France, assignor to Ilgenfritz Nurseries, Inc., Monroe, Mich., a corporation of Michigan Application December 3, 1958, Serial No. 778,044

1 Claim. (Cl. 47—61)

The present invention relates to a new and distinct variety of rose plant of the hybrid tea class, which was originated by me by crossing the variety "Charlotte Armstrong" (U.S. Plant Patent No. 455) with the variety "Baiser" (unpatented).

As the result of this breeding, I have produced a new variety of rose plant which is distinguished from its parents, as well as all other varieties of its class of which I am aware, and is particularly characterized as to novelty by the unique combination of the following outstanding characteristics:

(1) Strong and upright habits of plant growth;

(2) Good resistance to mildew and blackspot;

(3) Good bud form and a somewhat camellia-shaped form of the blooms;

(4) A distinctive two-toned rose and white general color tonality of the blooms; and (5) Good persistence of the flower color until the petals fall.

Asexual reproduction of my new variety by budding, as performed in France, as well as at Monroe, Michigan, U.S.A., shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of the new variety, with color terminology in accordance with the Horticultural Colour Chart issued by the British Colour Council in collaboration with The Royal Horticultural Society, except where general color terms of ordinary dictionary significance are obvious:

Type: Hardy; tall; bush; outdoor; seedling; for garden decoration.

Class: Hybrid tea.

Breeding: Seedling.

*Seed parent.*—"Charlotte Armstrong."

*Pollen parent.*—"Baiser."

Propagation: Holds its distinguishing characteristics through succeeding propagations by budding.

*Flower*

Locality where grown and observed: Monroe, Michigan, U.S.A.

Continuity: Continuous.

Fragrance: Moderate. Nature—tea.

Flowers borne: Sometimes singly and sometimes 2 or 3 to stem; on strong stems of medium length.

Quantity of bloom: Abundant, outdoors.

Bud:

*Peduncle.*—Medium length; medium heavy; erect; stiff; entire; smooth; with few yellow hairs. Color—green-bronze.

*Before calyx breaks.*—Size — medium. Form — pointed; without foliaceous appendages; without foliaceous parts extending from the surface of the bud. Color—Lettuce Green, Plate 861.

*As calyx breaks.*—Color—Chrysanthemum Crimson, Plate 824/1.

*As first petal opens.*—Size—medium. Form—short; ovoid. Color: outside—Cherry, Plate 722/3; inside—Cherry, Plate 722/3.

*Opening.*—Opens up well.

Bloom:

*Size (when fully open).*—From 4 inches to 5 inches.

*Petalage.*—Very double; arranged regularly. Number of petals under normal conditions—from 50 to 58.

*Form.*—Flat-cupped and full at first, but becoming flat-cupped; petals at first being loosely cupped, and remaining loosely cupped at maturity.

Petals:

*Texture.*—Thin; soft.

*Shape.*—Outside — obovate; scalloped; with one notch. Intermediate—obovate; scalloped; with one notch. Inside—obovate, with apex flat.

This description of a newly opened flower was made from a rose grown outdoors in the month of June at Monroe, Michigan, U.S.A.:

*Color.*—Outer petal: outside surface — Fuchsine Pink, Plate 627/2, shading to Primrose Yellow, Plate 601/3 at base; inside surface—Fuchsine Pink, Plate 627/1, shading to Primrose Yellow, Plate 601/3 at base. Intermediate petal: outside surface—Magenta Rose, Plate 027/1, shading to Primrose Yellow, Plate 601/3 at base; inside surface—Magenta Rose, Plate 027/1, shading to Primrose Yellow, Plate 601/3 at base. Inner petal: outside surface—Empire Yellow, Plate 603/3 at base, edged with Chinese Rose, Plate 024/1; inside surface—Chinese Rose, Plate 024/1.

This description was made from a rose that was open for 3 days outdoors in the month of June, at Monroe, Michigan, U.S.A.:

*Color.*—Outer petal: outside surface—white at base, edged with Fuchsine Pink, Plate 627/2; inside surface—Fuchsine Pink, Plate 627/1. Inner petal: outside surface—white at base, edged with Magenta Rose, Plate 027/3; inside surface—white at base, edged with Fuchsine Pink, Plate 627/2.

*General color effect.*—Newly opened flower—white at base, with remainder Rose Madder, Plate 23/2. 3-days open—Tyrian Rose, Plate 24/2.

*Behavior.*—Drop off cleanly; not affected by cold, hot, wet or dry weather.

*Flower longevity.*—On bush in garden—5 days in June. Cut roses grown outdoors and kept at living-room temperatures—6 days in June.

*Reproductive organs*

Stamens: Many; arranged irregularly about pistils. Color—red and brown.

Filaments: Medium length; most with anthers.

Anthers: All open at once. Color—brown.

Pollen: Color—gold.

Pistils: Medium number.

Styles: Uneven; medium length; medium caliper; very bunched.

Stigma: Color—red.

Ovaries: Some protruding from calyx.

Hips: Short; pointed; smooth; walls thick and fleshly. Color—green.

Sepals: Permanent; long; spear-shaped; curled. Color—green.

Seeds: Few; medium size.

*Plant*

Foliage:

*Leaves.*—Compound of 5 leaflets; normal abundance; medium large; heavy; leathery.

*Leaflets.*—Shape—ovoid, with apex acute. Margin—simply serrate.

*Color.*—Mature: upper surface—normal green; under surface—light green. Young: upper surface—bronze; under surface—red.

*Rachis (the supporting stem of the compound leaf).*—Medium caliper. Upper side—smooth; grooved. Under side—smooth.

*Stipules.*—Medium length; with points of medium length turning out at an angle of about 45°.

*Disease resistance.*—Resistant to mildew and blackspot, as determined by comparison with other varieties grown under comparable cultural conditions at Monroe, Michigan, U.S.A.

Growth:

*Habit.*—Upright.

*Growth.*—Vigorous.

*Canes.*—Heavy.

*Main stems.*—Color—dull green. Thorns—many; medium length; hooked downward; with long, narrow base. Prickles—none. Hairs—none.

*Branches.*—Color—dull. Thorns—many; medium length; hooked downward; with long, narrow base. Prickles—none. Hairs—none.

*New shoots.*—Color—dull bronze. Thorns—few; short; hooked downward; with long, narrow base. Prickles—none. Hairs—none.

I claim:

A new and distinct variety of rose plant of the hybrid tea class, substantially as herein shown and described, characterized particularly as to novelty by the unique combination of strong and upright habits of plant growth, good resistance to mildew and blackspot, good bud form, a somewhat camellia-shaped form of the blooms, a distinctive two-toned rose and white general color tonality of the blooms, and good persistence of the flower color until the petals fall.

No references cited.